(12) United States Patent
Langley et al.

(10) Patent No.: US 8,128,603 B2
(45) Date of Patent: Mar. 6, 2012

(54) PEN-TYPE INJECTOR HAVING AN ELECTRONIC CONTROL UNIT

(76) Inventors: Christopher Nigel Langley, Leamington Spa (GB); Shane Alistair Day, Warwick (GB); Robert Frederick Veasey, Leamington Spa (GB); Robert Woolston, Warwick (GB)

( * ) Notice: Subject to any disclaimer, the term of this patent is extended or adjusted under 35 U.S.C. 154(b) by 2081 days.

(21) Appl. No.: 10/433,643

(22) PCT Filed: Dec. 21, 2001

(86) PCT No.: PCT/GB01/05693
§ 371 (c)(1), (2), (4) Date: Jun. 6, 2003

(87) PCT Pub. No.: WO02/058766
PCT Pub. Date: Aug. 1, 2002

(65) Prior Publication Data
US 2004/0122355 A1    Jun. 24, 2004

(30) Foreign Application Priority Data

Dec. 22, 2000    (GB) .................................. 0031466.6

(51) Int. Cl.
*A61M 5/00*    (2006.01)
(52) U.S. Cl. .......................................... 604/181; 604/71
(58) Field of Classification Search .............. 604/65–72, 604/131, 207, 220, 197, 181, 187
See application file for complete search history.

(56) References Cited

U.S. PATENT DOCUMENTS

| | | | |
|---|---|---|---|
| 4,529,401 A | 7/1985 | Leslie et al. | |
| 5,514,097 A | 5/1996 | Knauer | |
| 5,868,710 A | 2/1999 | Battiato et al. | |
| 5,928,201 A | 7/1999 | Poulsen et al. | |
| 6,248,090 B1 * | 6/2001 | Jensen et al. | 604/67 |
| 6,299,601 B1 * | 10/2001 | Hjertman | 604/131 |
| 6,582,404 B1 * | 6/2003 | Klitgaard et al. | 604/181 |
| 2004/0054318 A1 * | 3/2004 | Langley et al. | 604/67 |

FOREIGN PATENT DOCUMENTS

| | | |
|---|---|---|
| DE | 299 18 149 U1 | 2/2000 |
| WO | WO 93/02720 | 2/1993 |
| WO | WO 01/26710 A2 | 4/2001 |

* cited by examiner

*Primary Examiner* — Jackie Ho
*Assistant Examiner* — Phillip Gray
(74) *Attorney, Agent, or Firm* — Oliff & Berridge, PLC

(57) ABSTRACT

An injection device of the kind having a main housing (4) is disclosed and includes a drive mechanism (42) to expel selectively a dose of medicament from a medicament cartridge (40) through a needle unit (22) and an electronic control unit to control the drive mechanism (42). The injection device further comprises a prime button (26) which causes a prime signal to be sent to the electronic control unit, the electronic control unit actuating the drive mechanism (42) to expel a predetermined small dose of medicament on receipt of the prime signal. In this way removal of entrapped air from the medicament cartridge (40) is obtained.

3 Claims, 3 Drawing Sheets

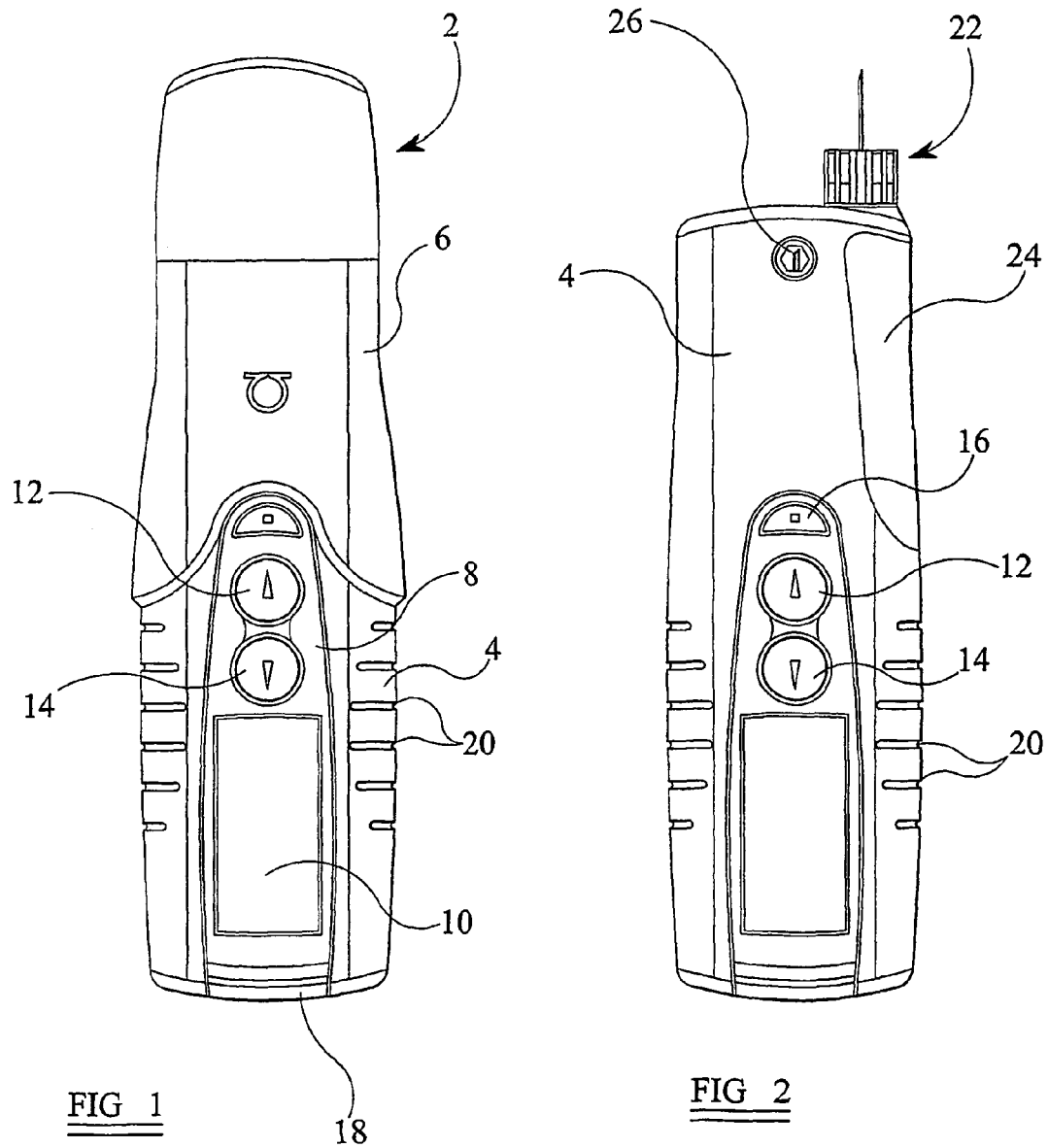

PEN-TYPE INJECTOR HAVING AN ELECTRONIC CONTROL UNIT

This application is related to U.S. patent application Ser. No. 10/433,642, filed Jun. 6, 2003.

The present invention relates to improvements in an injection device, and in particular to improvements in a portable injection device for dispensing controlled quantities of a medicament.

Typically such injection devices are used by those suffering from diabetes to administer a dose of insulin or insulin-type medicine to themselves. It will be understood that such injection devices are suitable for the injection of other medicines.

At one time, such doses were administered by use of a disposable syringe; the syringe first being filled from a separate phial or other container and then used to inject the dose. However, there were a number of difficulties in such an arrangement. In particular, such an arrangement was not suitable for the infirm. For others, the social stigma associated with such syringes made their public use problematic.

To overcome these difficulties a number of so-called pen-type injectors have been developed. These devices are small, being capable of being carried in a jacket pocket or the like and allow a number of doses to be obtained from a cartridge or ampoule contained within the injector. The present invention has particular application to such pen-type injectors.

While such pen-type injectors are a considerable improvement upon disposable hypodermic syringes, problems nevertheless remain. It is an advantage of the present invention that it eliminates, or at least substantially reduces such problems. The present invention also provides for improved ease of use and improved interaction with a user.

The invention will now be described, by way of example only, with reference to the accompanying drawings; in which:

FIG. 1 shows a plan view of a pen-type injector in accordance with the present invention;

FIG. 2 shows a similar view to FIG. 1 with an end cap of the injector omitted;

Figure 3:
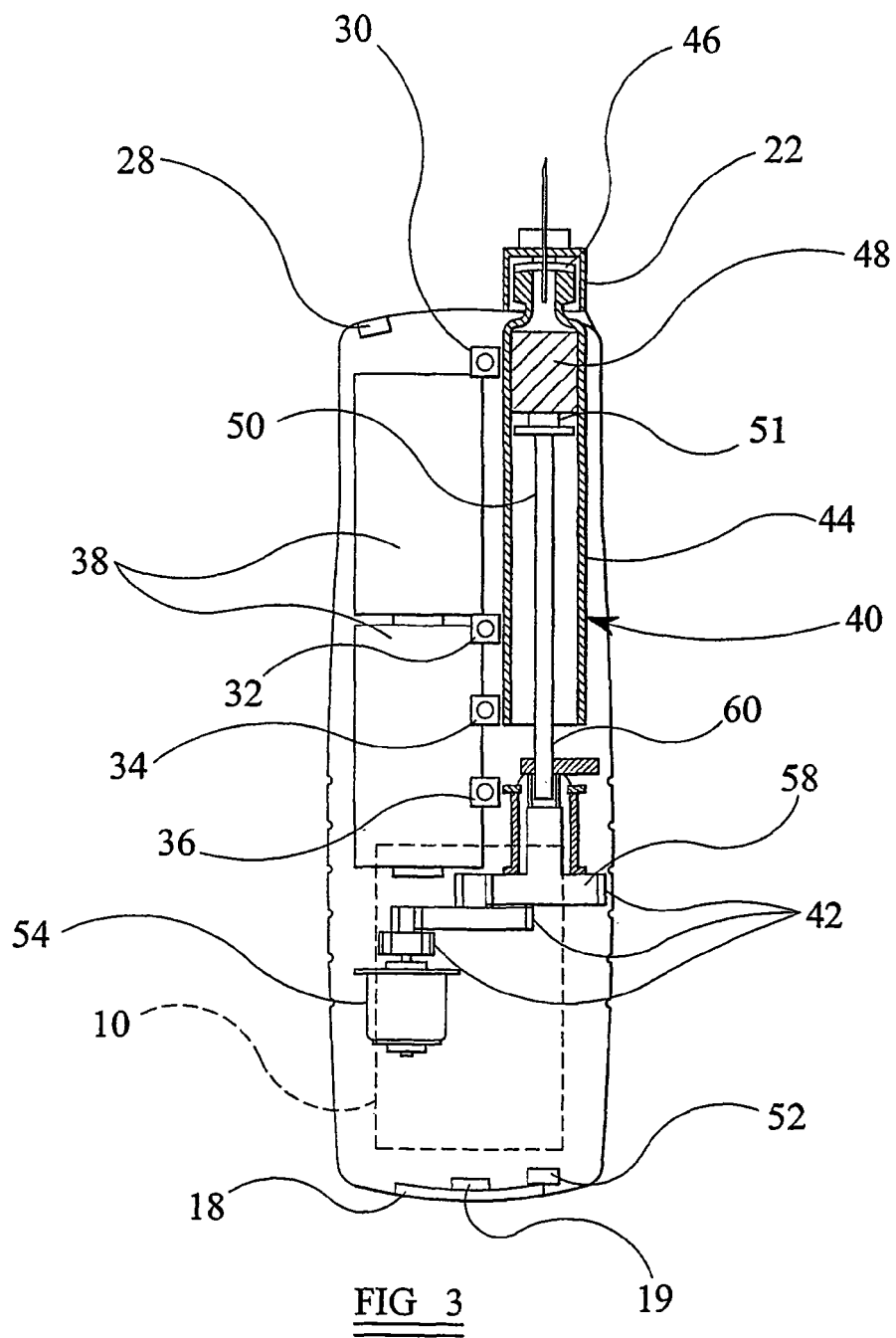
FIG. 3 shows a cross-sectional view of the injector of FIGS. 1 and 2.
Figure 3A:
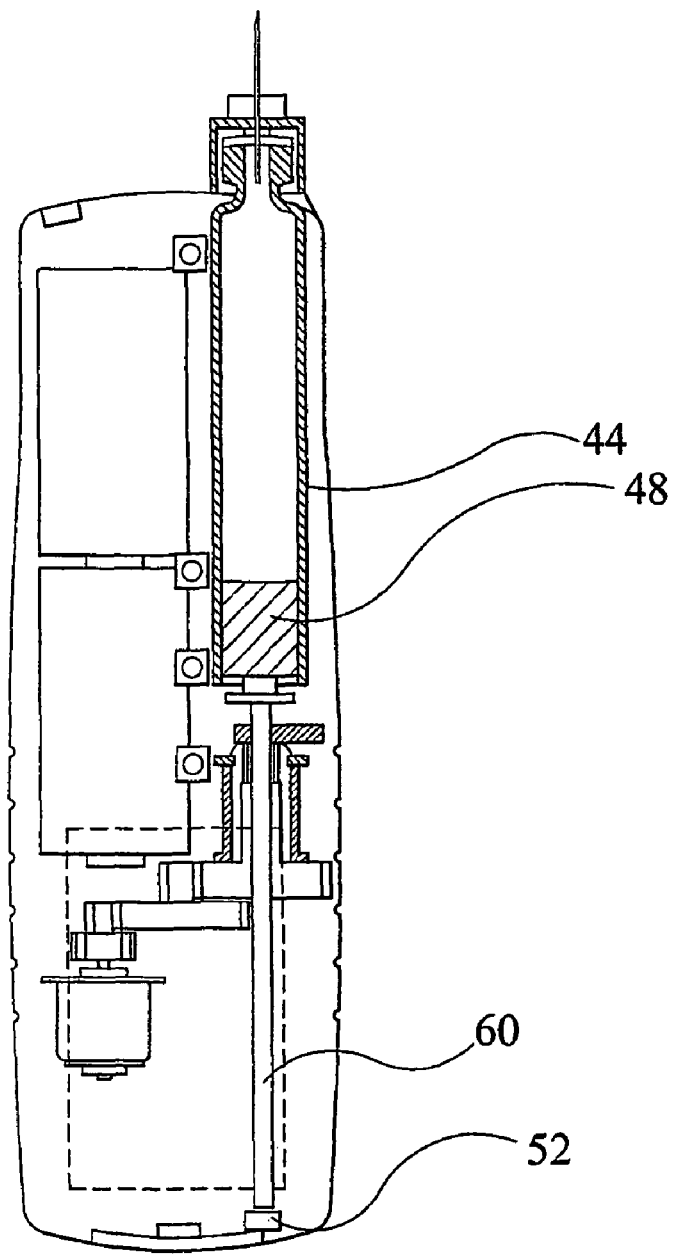
FIG. 3A shows a view similar to that of FIG. 3 with a filled cartridge in the injector.

Referring first to FIGS. 1 to 3, there can be seen a pen-type injector 2 in accordance with the present invention. The injector 2 comprises a main housing 4 to which is releasably secured an end cap or cover 6.

At a first end of the main housing 4 there is provided a control panel region 8. This region includes a display panel 10, typically a LCD display, and a first dose button 12 and a second dose button 14, the first and second dose buttons being operated to increase or decrease a dose of medicament to be delivered. The control panel region 10 in the illustrated embodiment also includes an arm button 16.

At the first end of the main housing there is also provided a dispense button 18. Preferably, when not depressed, the dispense button 18 is flush with the main housing 4.

Along a longitudinal axis of the injector 2, to each side of the control panel region 10 are provided a number of grooves or recesses 20. These aid in the gripping of the injector 2 by a user.

At a second end of the main housing 4 a needle unit 22 is releasably secured to the main housing. The second end of the main housing 4 is also provided with a shaped portion 24.

In use a cartridge 40 or ampoule of medicament is stored in the housing 4 behind the shaped portion 24. For preference, the shaped portion is transparent to permit the cartridge 40 to be seen by a user.

A prime button 26 is also provided on the second end of the housing 4. It will be understood that when the end cap 6 is in place over the second end of the housing, it will not be possible inadvertently to depress the prime button 26 or to be pricked by the needle unit 22. A cover detection switch 28 may also be included at the second end of the main housing 4 to detect whether the end cap or cover 6 is in place or not.

In FIG. 3, there can be seen a priming contact 30, an arm contact 32, a first dose contact 34 and a second dose contact 36 corresponding to the respective buttons. A dispense contact 19 corresponding to the dispense button 18 is also shown.

With reference to FIG. 3 it may be seen that there is provided a suitable location for a power source 38 such as a battery or batteries. There is also a suitable region in which a cartridge 40 or ampoule of medicament is to be located. This region may be accessed by way of the removable shaped portion 24 of the main housing 4 to allow for replacement of the cartridge 40 or ampoule as required by the user.

In a third region of the main housing 4 there is provided a drive mechanism 42 which operates from the power source 38 and acts upon the cartridge 40 or ampoule of medicament.

The cartridge 40 or ampoule comprises a container 44 or sleeve closed at one end by a cover 46 at a head end thereof, and sealed at the other by a movable bung 48 or stopper. When in position, the needle unit 22 pierces the cover 46 and movement of the bung 48 towards the cover 46 will cause the medicament contained within the cartridge 40 or ampoule to be expelled. The cartridge may be a 3 ml cartridge in accordance with ISO/FDIS 11608 Part 3, or any other suitable cartridge to suit the injector.

Movement of the bung 48 or stopper is caused by movement of a piston or plunger 50 forming a part of the drive mechanism 42. The piston or plunger 50 is movable between a first fully withdrawn position (not shown) which allows for the replacement of the cartridge 40 or ampoule and a second fully extended portion in which as much medicament as possible has been expelled from the cartridge 40 or ampoule. An end stop switch 52 may be provided in the main housing 4 to detect when the piston 50 is in the fully withdrawn position. Tripping of the switch end stop 52 may release a catch or other fastening device to allow access to the main housing 4 for replacement of the cartridge 40.

The drive mechanism 42 is operated by a motor 54 under the control of an electronic lo control unit (not shown). The motor 54 should be reversible in order ,o allow the piston 50 to be moved between the first and second positions. In FIG. 3, the motor 54 can be seen to drive the piston 50 by way of a gear train 42, such that rotation of a third rotor 58 causes the piston 50 to be moved in relation to the third rotor 58.

Preferably, the user can feel the vibration of the motor 54 and the associated drive mechanism 42 and/or hear them in operation. In this way an added degree of confidence in the fact of the operation of the injector 2 is provided to the user.

The functionality of a pen-type injector in accordance with the present invention will now be described, in particular with reference to FIGS. 1, 2 and 3.

The injector 2 is provided with an electronic control unit. The electronic control unit is coupled both to the drive mechanism and a user interface. The user interface includes the display panel 10 as well as the user operable buttons (and associated contacts). The electronic control unit is microprocessor based. Either volatile or non-volatile memory may be used for storage of 'dose history' and patient specific information. It will be understood that depression of the user operated buttons will cause associated signals to be sent to the electronic control unit, that is when the prime button 26 is depressed a prime signal will be sent to the electronic control unit.

The electronic control unit is preferably powered from the injector power source 38.

The injector 2 preferably also includes a port for communication between the electronic control unit and an external apparatus such as a personal computer.

The injector 2 also has a priming detection facility, (such as a tilt switch or accelerometer) to identify when the injector 2 is inverted. On detection of an inverted position (needle up) the injector 2 will automatically change state to be ready for priming. Priming may be initiated by depression of the prime button 26 to cause a fixed small dispense action. The electronic control unit may cause a speaker to sound when the prime button 26 is depressed.

The prime button 26 is inactive at all other times. When the prime button 26 is active, all other buttons in the control panel region are inactive, that is those buttons which are to be used to set or dispense a dose. In other words, when the prime button 26 is active, the electronic control unit or processor will only actuate the drive mechanism 42 to cause a fixed small dispense action The electronic control unit may cause a speaker to sound when the arm button 16 is depressed for a sufficient period of time to provide audible feedback for the user.

The function of the arm button 16 is to make the dose button 18 active. The arm button is preferably held down for a predetermined period of time before the injector 2 becomes armed. The armed status may additionally be shown on the display panel 10. The functionality of the arm button is preferably linked to the cover detection switch 28 such that the arm button 16 will only function to arm the injector 2 when the cover 6 is not present.

Additionally, in a preferred embodiment, a clock within the electronic control unit will detect whether the dose button 18 has been pressed within a specified time interval following arming of the injector 2. If the dose button 18 has not been depressed within the specified time interval the electronic control unit will disarm the injector 2. Alternatively, if the arm button is depressed a second time within a predetermined time period by the user, the injector will be disabled.

In an alternative embodiment, the dose button 18 may function as both a prime button and the dose button. When the priming detector is actuated, by the injector 2 being oriented needle up, the dose button 18 would change function to that of the prime button of the previous embodiment.

The buttons of the injector 2 are preferably tactile in nature to provide sensory feedback to the user.

The display panel 10 is typically an LCD display and will provide alphanumeric and graphical information relating to the operation of the device. The display panel 10 preferably indicates the selected dose quantity, the previous dose quantity and the time elapsed since the previous dose was administered. Typically, the time elapsed since the previous dose is limited to a time period within the preceding 48 hours, though other time periods are possible.

Additional information which may be displayed includes:
that the injector is armed and ready to dispense (graphical)
that the injector is dispensing (graphical)
that the injector has dispensed the selected dose and that a user should wait before removing the needle from their body
that this waiting period has elapsed
the dose history, typically for the last 48 hours, in terms of the dosage taken and the elapsed time between doses
the quantity of medicament remaining in the cartridge, preferably in terms of dosage units of the medicament.
that the device is in the priming position (either in addition to or instead of the acoustic indication noted above)
the speaker volume setting, for example high, low or muted.
that the injector is nearing the end of its life (for example a battery power level indication—graphical or countdown in terms of the number of days or complete operating cycles to a predetermined expiry of the product life—alphanumeric).
that the needle is probably blocked
that replacement of the cartridge 40 is in progress
that the dose selected is the maximum available in the cartridge 40
that the maximum dose available is less than the dose expected.

The display panel 10 may offer a user a choice of language options as appropriate for the market and/or user. The text displayed may include that noted above and/or further information. The language option may be pre-programmed or selectable by a user. The user may preferably select the language option by means of a menu provided on the display panel 10.

The currently selected dose value, the previously used dose value and the time (in hours) since the previous dose was dispensed, may all be shown clearly at the same time, in large, easy-to-read characters on the display. Preferably, the display is also provided with a backlight.

The display 10 preferably provides a graphical indication that the selected dose is being dispensed. This may be achieved, for example, as either an animated graphic or a countdown (or a combination of both).

The control buttons have a number of functions. The dose buttons 12,14 allow a user to select a desired dosage. The dose arm button 16 allows a user to confirm selection of a desired dosage. The first dose button can increment the dosage level and the second dose button can decrement the dosage level. The dose dialing buttons 12,14 may be pressed down (and held for a short time, 1-2 seconds) to re-set a dose value to zero. The user can then dial up (or down) in single (or half) increments.

The dose dialing buttons 12,14 are intended to be pressed once for a single (or half) increment in the selected dose value. In an alternative embodiment, pressing and holding one of the buttons will cause the dose value to start to scroll (up or down) in order to change the dose size more rapidly.

The dispense button 18 allows a user to initiate dispensing of the dosage. The primer button 26 dispenses a unit of dosage from the cartridge 40. Thus, if any air is trapped in the injector 2 this can be expelled by use of the prime button 26. A door release catch is provided to allow access to the cartridge 40.

The invention claimed is:

1. An injection device of the kind having a main housing including:
    a drive mechanism to expel selectively a dose of medicament from a medicament cartridge through a needle unit;
    an electronic control unit to control the drive mechanism, wherein the injection device further comprises a prime button which causes a prime signal to be sent to the electronic control unit, the electronic control unit actuating the drive mechanism to expel a predetermined dose of medicament on receipt of the prime signal; and a cover adapted to cover the needle unit and a part of the main housing, wherein the prime button is located within the part of the main housing adapted to be covered by the cover.

2. The injection device according to claim 1, wherein the injection device further comprises a priming detection means to sense the orientation of the injection device, and the electronic control unit will only cause the drive mechanism to operate in response to a priming signal when the injection device is in predetermined orientation.

3. The injection device according to claim 2, wherein the injection device further comprises additional buttons which in use generate further signals to which the electronic control unit optionally responds, the electronic control unit not responding to the further signals when the injection device is in the predetermined orientation.

* * * * *